(12) United States Patent
Tatonetti

(10) Patent No.: US 11,229,727 B2
(45) Date of Patent: Jan. 25, 2022

(54) INTELLIGENT ADJUSTMENT OF DIALYSIS MACHINE OPERATIONS

(71) Applicant: Thomas Tatonetti, Brooklyn, NY (US)

(72) Inventor: Thomas Tatonetti, Brooklyn, NY (US)

(73) Assignee: KATA Gardner Technologies, Brooklyn, NY (US)

(*) Notice: Subject to any disclaimer, the term of this patent is extended or adjusted under 35 U.S.C. 154(b) by 23 days.

(21) Appl. No.: 16/535,036

(22) Filed: Aug. 7, 2019

(65) Prior Publication Data

US 2019/0365976 A1 Dec. 5, 2019

(51) Int. Cl.
| | |
|---|---|
| *A61M 1/16* | (2006.01) |
| *A61M 1/36* | (2006.01) |
| *A61M 1/34* | (2006.01) |
| A61M 1/28 | (2006.01) |

(52) U.S. Cl.
CPC ........ *A61M 1/1603* (2014.02); *A61M 1/3403* (2014.02); *A61M 1/3639* (2013.01); *A61M 1/1656* (2013.01); *A61M 1/287* (2013.01); *A61M 2205/3331* (2013.01); *A61M 2205/3368* (2013.01); *A61M 2205/50* (2013.01)

(58) Field of Classification Search
None
See application file for complete search history.

(56) References Cited

U.S. PATENT DOCUMENTS

| | | | |
|---|---|---|---|
| 2015/0045713 A1* | 2/2015 | Attalah | A61M 1/14 604/5.04 |
| 2018/0043075 A1* | 2/2018 | Gerber | A61M 1/1609 |
| 2018/0043076 A1* | 2/2018 | Gerber | A61M 1/287 |

* cited by examiner

*Primary Examiner* — Richard C Gurtowski
(74) *Attorney, Agent, or Firm* — Tatonetti IP

(57) ABSTRACT

A remote service is implemented to automatically aggregate data across hemodialysis patients and determine updated treatment options for patients to increase well-being and optimize performance of the hemodialysis machines. Patients or caregivers operating a hemodialysis machine or a local or remote user computing device associated with the hemodialysis machine can provide feedback regarding the patient's well-being to the remote service. The feedback can be provided at any of one or more times pre-treatment, during treatment, or post-treatment. Furthermore, the hemodialysis machine can be configured with one or more sensors that transmit data pertaining to device state of the hemodialysis machine, such as information about blood, dialysate used, saline solution, pump pressure, air trap and air detector, hemodialysis machine information (e.g., make and model), etc.

17 Claims, 17 Drawing Sheets

1300

1400

INTELLIGENT ADJUSTMENT OF DIALYSIS MACHINE OPERATIONS

BACKGROUND

Hemodialysis machines are utilized to filter a patient's blood due to renal failure, in which numerous components and functions are utilized by the dialysis machine during filtration. The components and functionality for a given hemodialysis machine can vary by patient, such as a rate at which blood is pumped, composition of dialysate, among other variances. In some scenarios, patients can experience discomfort during or after treatment, such as overall discomfort, muscle cramps, dizziness, etc. As portable dialysis treatments become increasingly popular, adjusting treatment can provide increased patient comfort, experience, and well-being.

SUMMARY

A remote service is configured to automatically aggregate data across hemodialysis patients and machines, recognize patterns, and determine updated treatment options for patients to increase well-being and optimize performance of the hemodialysis machine. Patients, caregivers, or otherwise users operating a hemodialysis machine or a local or remote computing device associated with the hemodialysis machine can provide feedback regarding the patient's well-being to the remote service. Use of the term "user" herein can refer to the patient or a caregiver operating the hemodialysis machine or computing device for the patient. The feedback can be provided at any of one or more times including pre-treatment, during treatment, or post-treatment. Furthermore, the hemodialysis machine can be configured with one or more sensors that transmit data pertaining to device state of the hemodialysis machine, such as information about blood, dialysate used, saline solution, pump pressure, air trap and detector, hemodialysis machine information (e.g., make and model), etc.

Upon receiving the user's feedback and crowd-sourced feedback from other hemodialysis users, the remote service can identify patterns in the data. The remote service can utilize an artificial intelligence engine (AI engine) to identify patterns and provide useful predictions for patients' treatments and hemodialysis machine configurations. The AI engine can ingest the data (e.g., user feedback, device state information, etc.), clean, prepare and manipulate the data, train a model, test the model, and then deploy a generated predictive model. In some exemplary scenarios, the remote service can remotely control and automatically adjust functions or operations of the hemodialysis machine (e.g., dialysate composition, temperature of dialysate, etc.), or can transmit a notification to the patient or caregiver regarding a recommended change in treatment or change in the hemodialysis machine's operation. In one exemplary scenario, the remote service can automatically adjust a concentration of ingredients in dialysate (e.g., the bicarbonate, acid, or water) when like patients, using a similar dialysate composition, are experiencing common symptoms. The notification can be transmitted and displayed on a display of the hemodialysis machine itself, or on a user computing device remote from the machine.

In some implementations, the hemodialysis machine can utilize processors or System on a Chips (SoCs) to control operations of the hemodialysis machine. For example, an SoC may be specifically configured to control temperature or composition of dialysate. The remote service can transmit a command to the SoC or processor associated with the hemodialysis machine to adjust operations in situations in which the remote service automatically controls machine operations.

Utilization of crowd-sourced feedback and the remote service's AI engine enables both experienced and inexperienced users of hemodialysis machines to benefit from pattern recognition techniques and an optimized machine. Furthermore, in some situations, the remote service can recognize faults with the hemodialysis machine and thereby remotely correct the issue or transmit a notification to the user for correction. Optimizing the hemodialysis machine's operations can prolong the machine's life, optimize its settings, reduce the possibility of component or machine failure, and overall increase performance of the machine, all while increasing user comfort, care, and well-being.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure. It will be appreciated that the above-described subject matter may be implemented as a computer-controlled apparatus, a computer process, a computing system, or as an article of manufacture such as one or more computer-readable storage media. These and various other features will be apparent from a reading of the following Detailed Description and a review of the associated drawings.

DESCRIPTION OF THE DRAWINGS

Like reference numerals indicate like elements in the drawings. Elements are not drawn to scale unless otherwise indicated.

DETAILED DESCRIPTION

Figure 1:
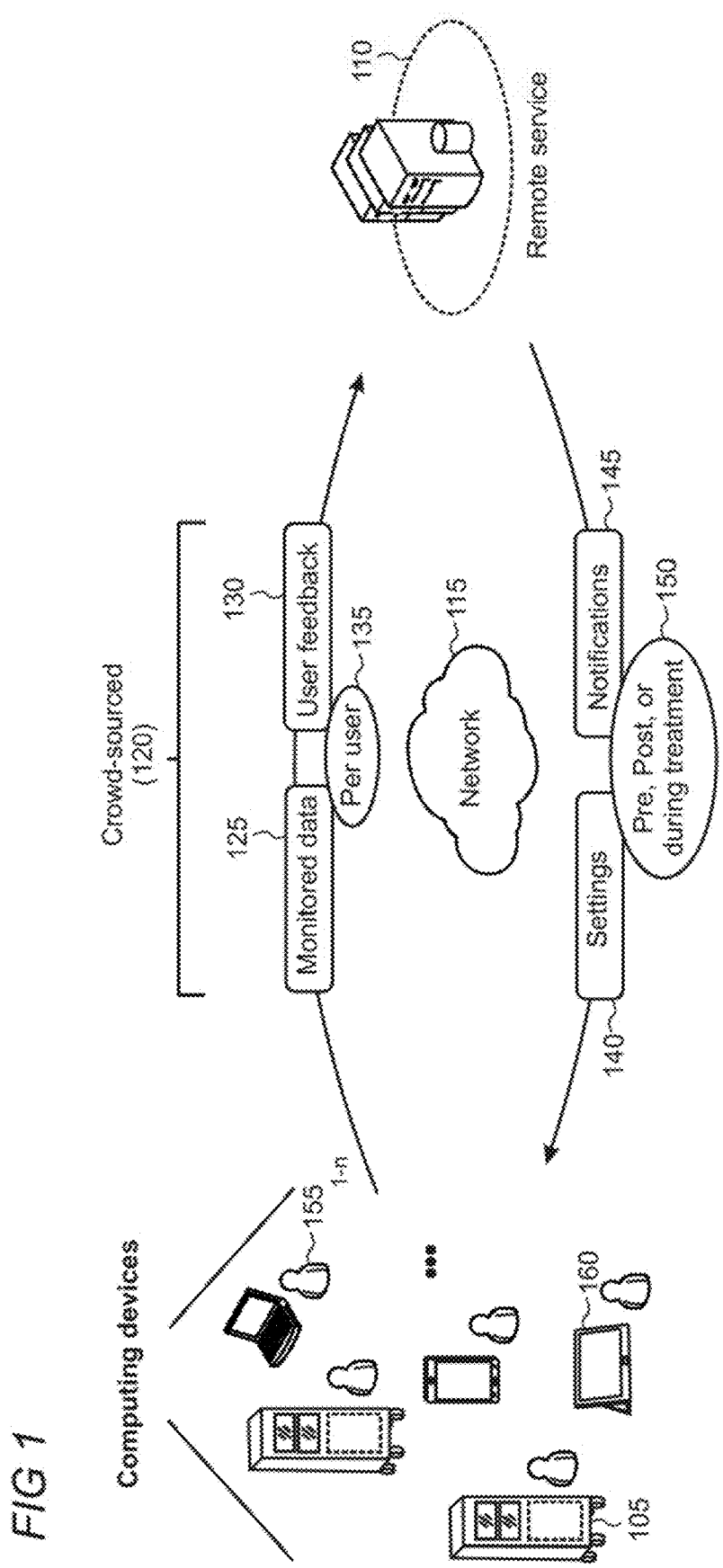
FIG. 1 shows an illustrative environment in which crowd-sourced data from hemodialysis machines and computing devices is utilized by the remote service to responsively transmit settings and/or notifications.

FIG. 1 shows an illustrative environment in which crowdsourced data from hemodialysis machines 105 and/or computing devices 160 are received and utilized by a remote service 110 to responsively transmit treatment settings 140 and notifications 145 to the hemodialysis machines or associated computing devices. Such transmissions can occur over the network 115, which can include any one or more of a local area network, wide area network, Internet, or World Wide Web.

On a per-user 135 basis, the hemodialysis machines 105 can monitor data surrounding treatment (e.g., utilized components and settings of the hemodialysis machine, patient information, etc.) for a patient 155 and transmit such data to the remote service 110. User feedback at the hemodialysis machines or associated computing devices can likewise be transmitted to the remote service. Collectively, the crowdsourced data 120 enables the remote service to analyze the data across many patients and treatment sessions. As discussed in greater detail below, the remote service can analyze the received data, develop new treatment plans, notifications, or operation adjustments based on each patient's unique situation, and transmit adjustments or notifications to the patient's respective hemodialysis machine. The signals can be transmitted pre-treatment, during treatment, or post treatment, as representatively shown by numeral 150.

Figure 2:
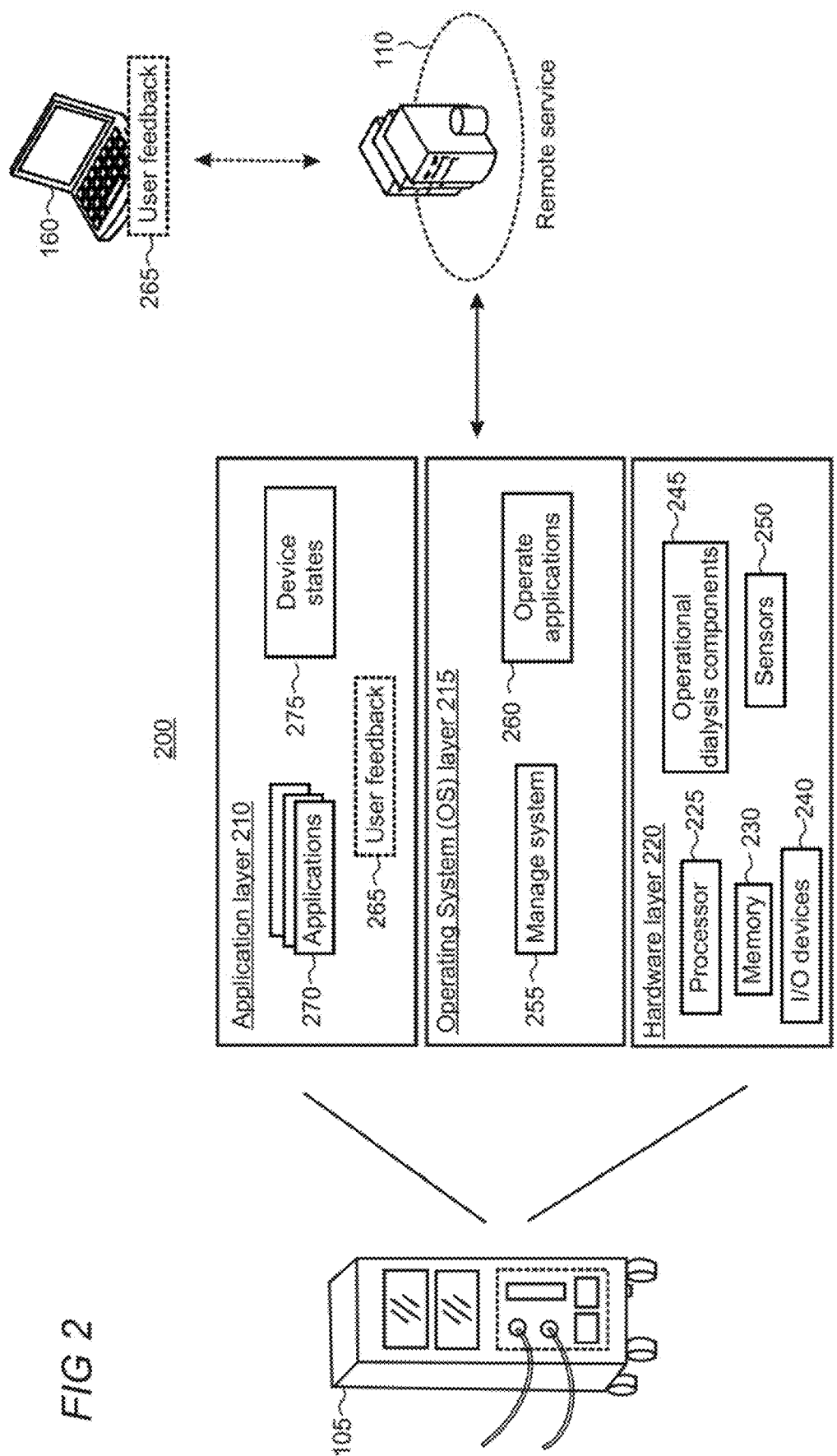
FIG. 2 shows a layered architecture of an illustrative hemodialysis machine.

FIG. 2 shows a simplified layered architecture 200 of the hemodialysis machine 105. The machine can include a hardware layer 220, operating system (OS) layer 215, and application layer 210. The hardware layer 215 provides an abstraction of the various hardware used by the host device 105 (e.g., input and output devices, networking and radio hardware, etc.) to the layers above it. In this illustrative example, the hardware layer supports processor(s) 225, memory 230, input/output devices (e.g., mouse, keyboard, display) 240, operational dialysis components 245, and sensors 250 for sensing operations of the hemodialysis machine (e.g., pump speed, blood or saline composition, etc.). A description of the operational dialysis components is discussed in greater detail with respect to FIG. 15. Although not shown, the hemodialysis machine can also include a network interface card (NIC) which enables a wired or wireless connection to the Internet, such as through a router. This can enable the hemodialysis machine to communicate with the remote service 110 (e.g., transmit data and feedback, receive settings and notifications, etc.). In some implementations, the hemodialysis machine can support short-range communications over Bluetooth™ or NFC (Near Field Communication), such as to a user's personal computing device (e.g., smartphone, tablet computer, personal computer (PC), laptop, etc.).

The application layer 210 in this illustrative example supports various applications 270, a device state application 275 that transmits information about the hemodialysis machine to the remote service, and a user feedback application 265 which enables input of user feedback into the hemodialysis machine and transmission to the remote service 110. In some implementations, the user's computing device 160 can be configured to receive user feedback and communicate with the remote service 110. Although the distinct applications are depicted in FIG. 2, the applications may alternatively operate within a same application, as a plugin to other applications or the OS, or interoperate with remotely executing code, such as with the remote service.

Although only certain applications are depicted in FIG. 2, any number of applications can be utilized by the hemodialysis machine. The applications are often implemented using locally executing code. In some cases, however, these applications can rely on services and/or remote code execution provided by remote servers or other computing platforms such as those supported by a service provider or other cloud-based resources (not shown).

The OS layer 215 supports, among other operations, managing system 255 and operating applications/programs 260. The OS layer may interoperate with the application and hardware layers in order to perform various functions and features.

Figure 3:
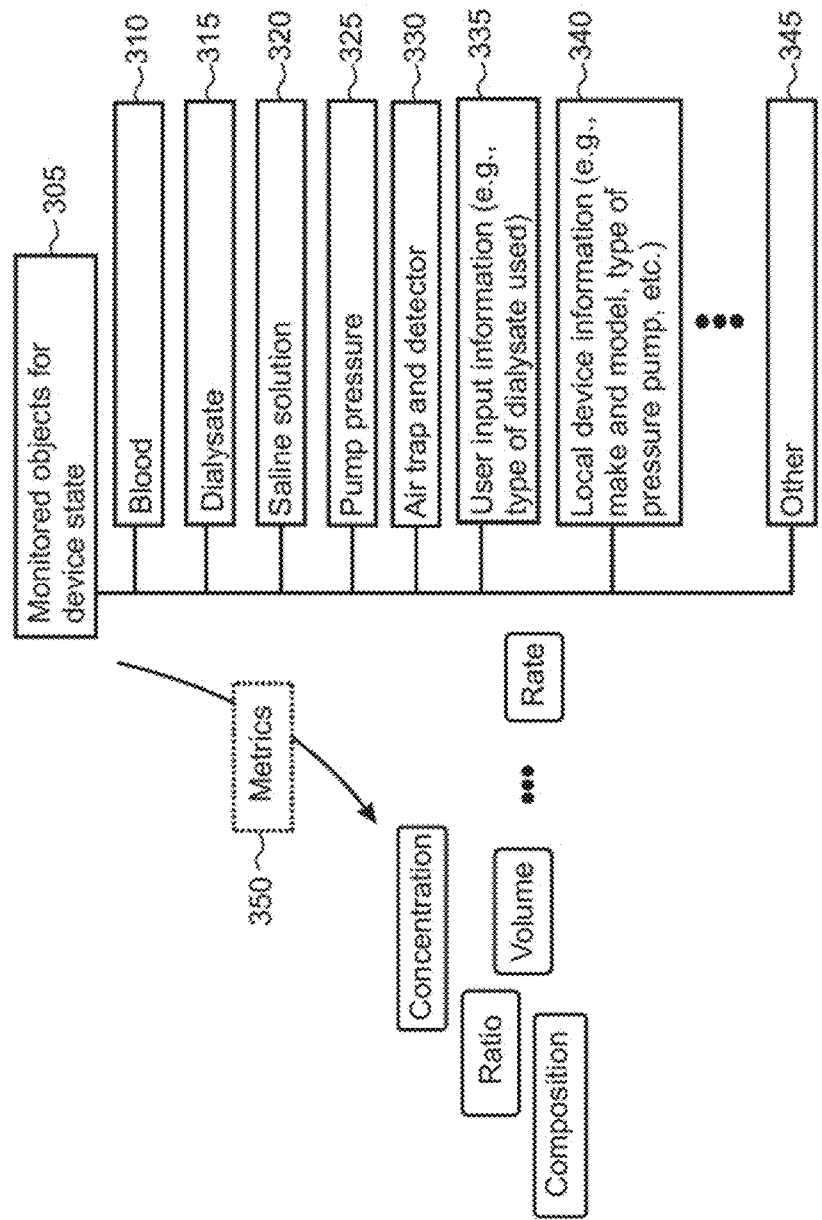
FIG. 3 shows a taxonomy of illustrative objects monitored by the remote service.

FIG. 3 shows a taxonomy of objects which the hemodialysis machine may monitor, such as using the device state application 275 (FIG. 2), as representatively shown by numeral 305. Exemplary and non-exhaustive objects can include blood 310, dialysate 315, saline solution 320, pump pressure 325, air trap and detector 330, user input information (e.g., type of dialysate used) 335, local device information (e.g., make and model, type of pressure pump, etc.) 340, and other features or components associated with the hemodialysis machine 105. The objects can be monitored according to one or more various metrics 350, such as a concentration (e.g., concentration of dialysate or blood), ratio, composition (e.g., composition of the dialysate), volume, rate (e.g., rate at which blood is pumped from the patient), among other metrics.

Figure 4:
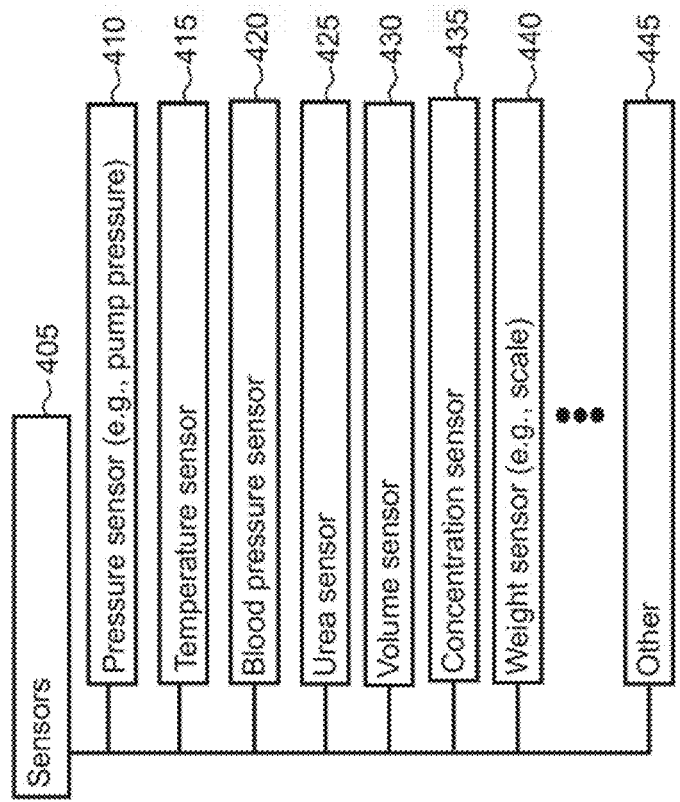
FIG. 4 shows a taxonomy of illustrative sensors implemented on hemodialysis machines.

FIG. 4 shows a taxonomy of sensors which may be implemented within the hemodialysis machine 105, as representatively shown by numeral 405. Exemplary and non-exhaustive sensors include a pressure sensor (e.g., for pump pressure) 410, temperature sensor 415 (e.g., for dialysate), blood pressure sensor 420, urea sensor 425, volume sensor 430, concentration sensor 435, weight sensor (e.g., a scale) 440, and other sensors 445. The sensors may be utilized to gather information and data about the hemodialysis machine, components within the machine, and its operations and transmit the gathered data to the remote service.

Figure 5:
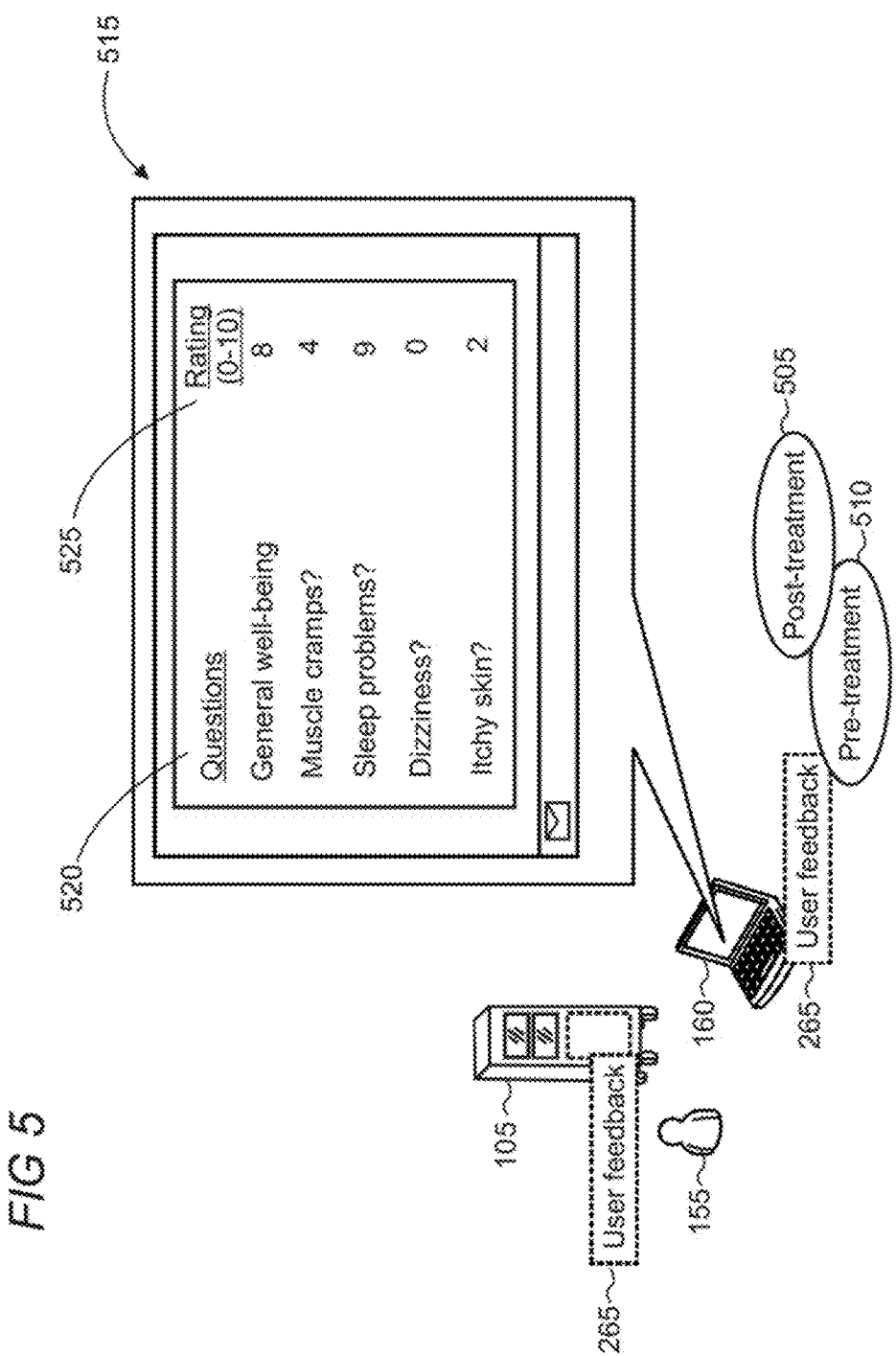
FIG. 5 shows an illustrative environment in which a user enters feedback into a user interface associated with the hemodialysis machine or computing device for transmission to a remote service.

FIG. 5 shows an illustrative user interface 515 associated with the user feedback application 265 on a display of either the computing device 160 or hemodialysis machine 105. The user interface depicts one possible feedback mechanism by which patients or medical providers can provide feedback to the remote service for analysis. In this illustrative example, questions 520 are posed, to which the patient can respond using a 0-10 rating, as representatively shown by numeral 525. That is, the patient can rate a degree of comfort or discomfort for each posed question. While a particular feedback style is depicted in FIG. 5, other forms of feedback are also possible, such as general user comments, radio buttons that indicate yes/no or the presence/absence of a condition, checkboxes, text boxes for input, etc. In some scenarios, the feedback may be in format that is consumable for processing by an artificial intelligence engine, such that the data is properly divided or separated (e.g., by commas). The data may be in the appropriate format upon users entering the data or may be reconfigured upon receipt at the remote service. The user can provide the feedback pre-treatment 510, post-treatment 505, or both.

Figure 6:
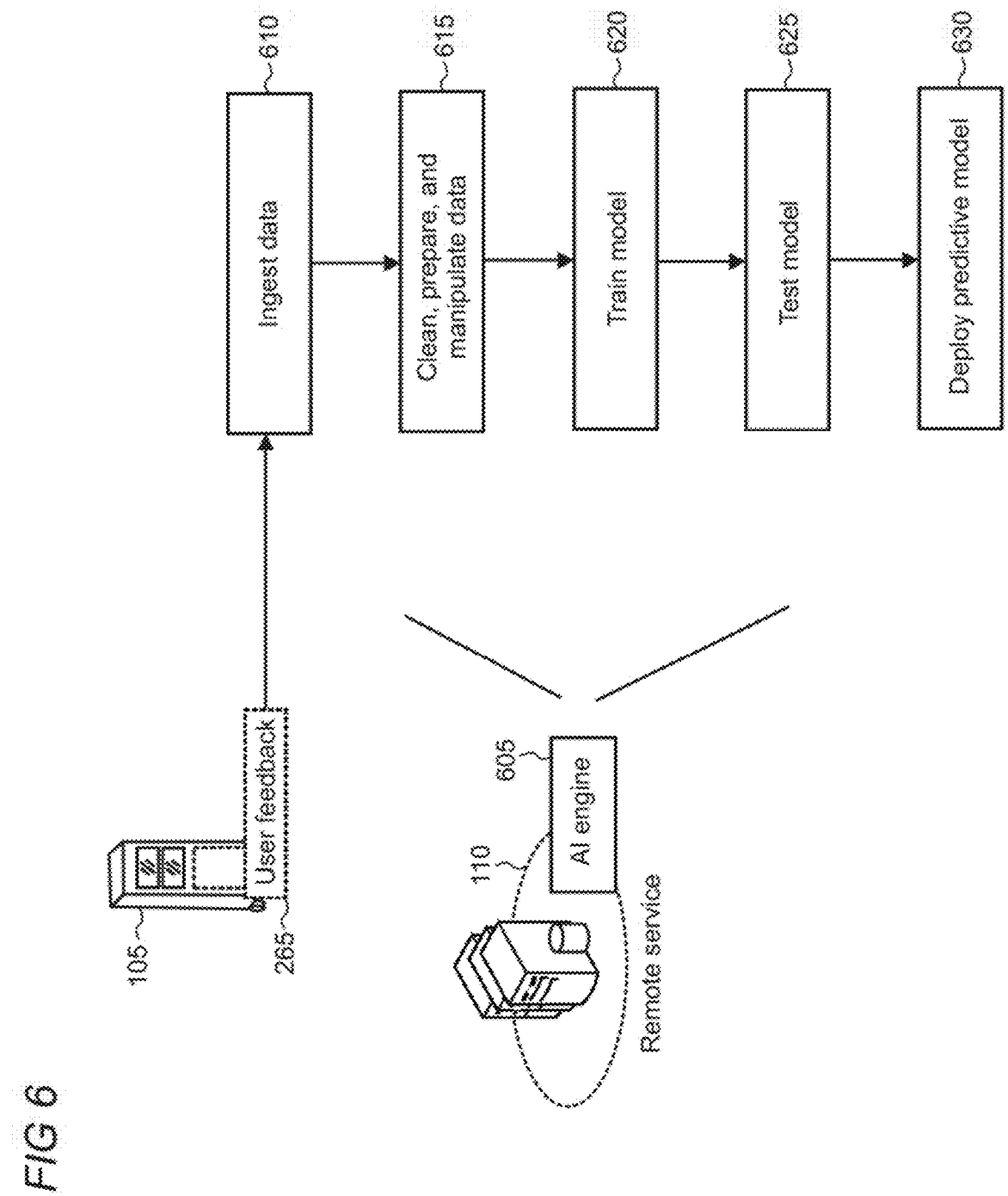
FIG. 6 shows an illustrative diagram in which an artificial intelligence (AI) engine associated with the remote service creates a predictive model using received data.

FIG. 6 shows an illustrative diagram in which the remote service 110 employs an artificial intelligence (AI) engine 605 to recognize patterns among hemodialysis patients. The AI engine utilizes an algorithm to develop a predictive model based on the crowd-sourced data. In step 610, the AI engine ingests the data 610 (e.g., the user feedback and device state information). In step 615, the AI engine may clean, prepare, and manipulate the data. For example, the data may be randomized, to reduce the possibility of an order affecting the machine learning process, and separated, between a training set for training the model and a testing set for testing the trained model. Other forms of data manipulation may be performed as well, such as normalization, error correction, and the like.

In steps 620 and 625, the AI engine trains and tests the model, respectively. The model training may be used to incrementally improve the model's ability to make accurate predictions. The model training may use the features contained in the data to form a matrix with weights and biases against the data. Random values within the data may be utilized to attempt prediction of the output based on those values. This process may repeat until a more accurate model is developed which can predict correct outputs. The model may subsequently be evaluated to determine if it meets some accuracy threshold (e.g., 70% or 80% accuracy), and then the predictive model will be deployed to make predictions at step 630.

While the AI engine is one method by which the remote service can develop pattern recognitions among the crowd-sourced data, other methods of pattern recognition are also possible. Such as using hard coded methods in an algorithm which creates correlations between a patient's experiences and conditions with the hemodialysis treatment information (FIG. 3).

Figure 7:
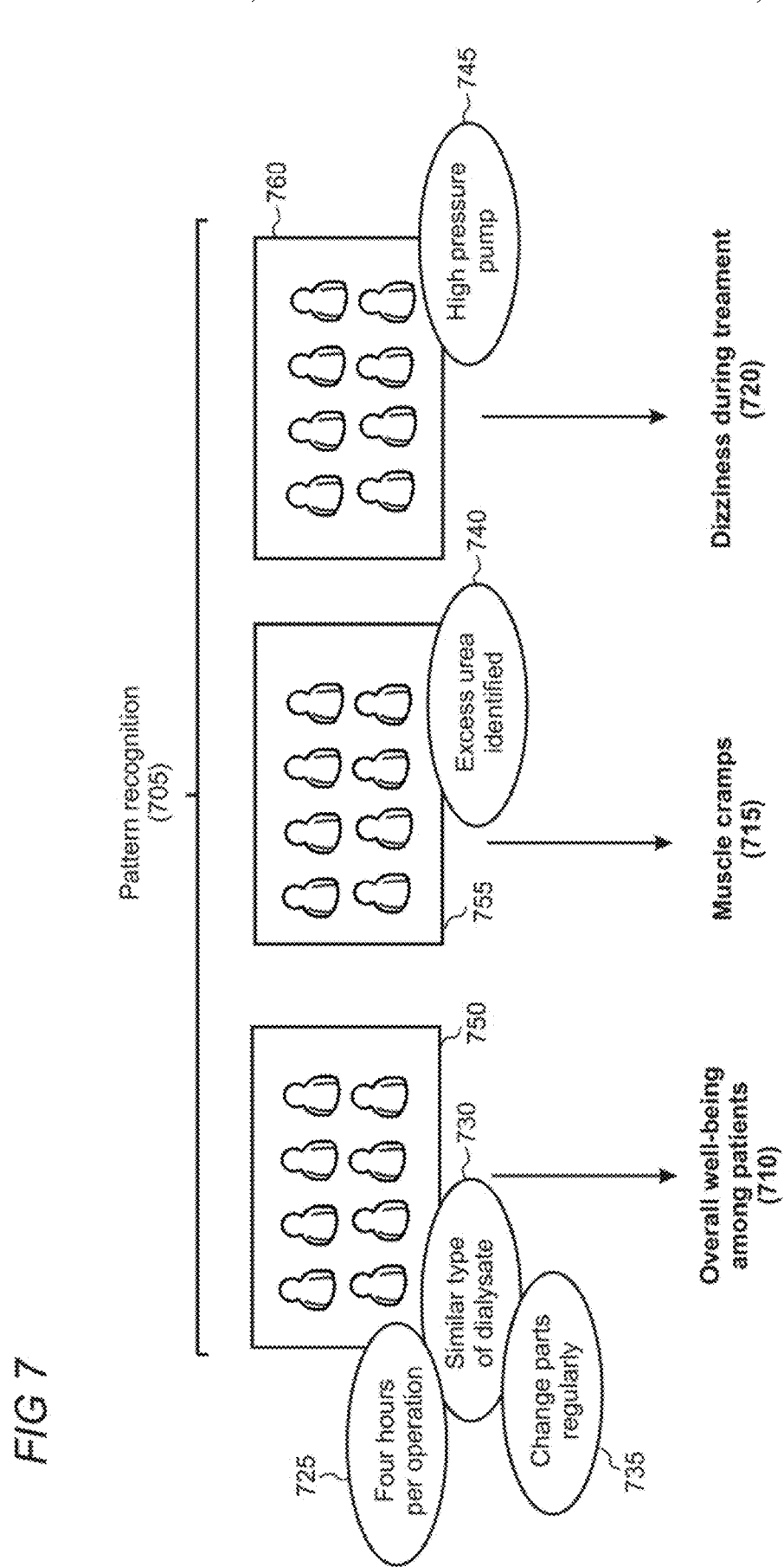
FIG. 7 shows an illustrative diagram in which the remote service performs pattern recognition on received user feedback and/or monitored data.

FIG. 7 shows an illustrative environment in which the remote service 110, upon receiving the feedback, recognizes patterns among the patients, as representatively shown by numeral 705. For example, the group of patients 650 may all experience overall well-being 710, in which the remote service recognizes that the patients spend four hours per hemodialysis treatment session 725, utilize similar types of dialysate 730, and change parts regularly 735. The remote service may have identified these commonalities among patients who are experiencing well-being. This data can be used when assessing patients who are having negative experiences with their treatment, in which the remote service can make an adjustment or transmit a notification to the user to make a change that comports with the setup of the group 750.

The remote service 110 may recognize that the group of patients 755 experiencing muscle cramps 715 may each be associated with an excess amount of urea 740, detected by a sensor in the hemodialysis machine. The remote service may recognize that the group of patients 760 may be experiencing dizziness during treatment 720, which is typically associated with high pressure pump 745, also detected by a sensor within the machine. Other examples of pattern recognition using the crowd-sourced data is also possible.

Figure 8:
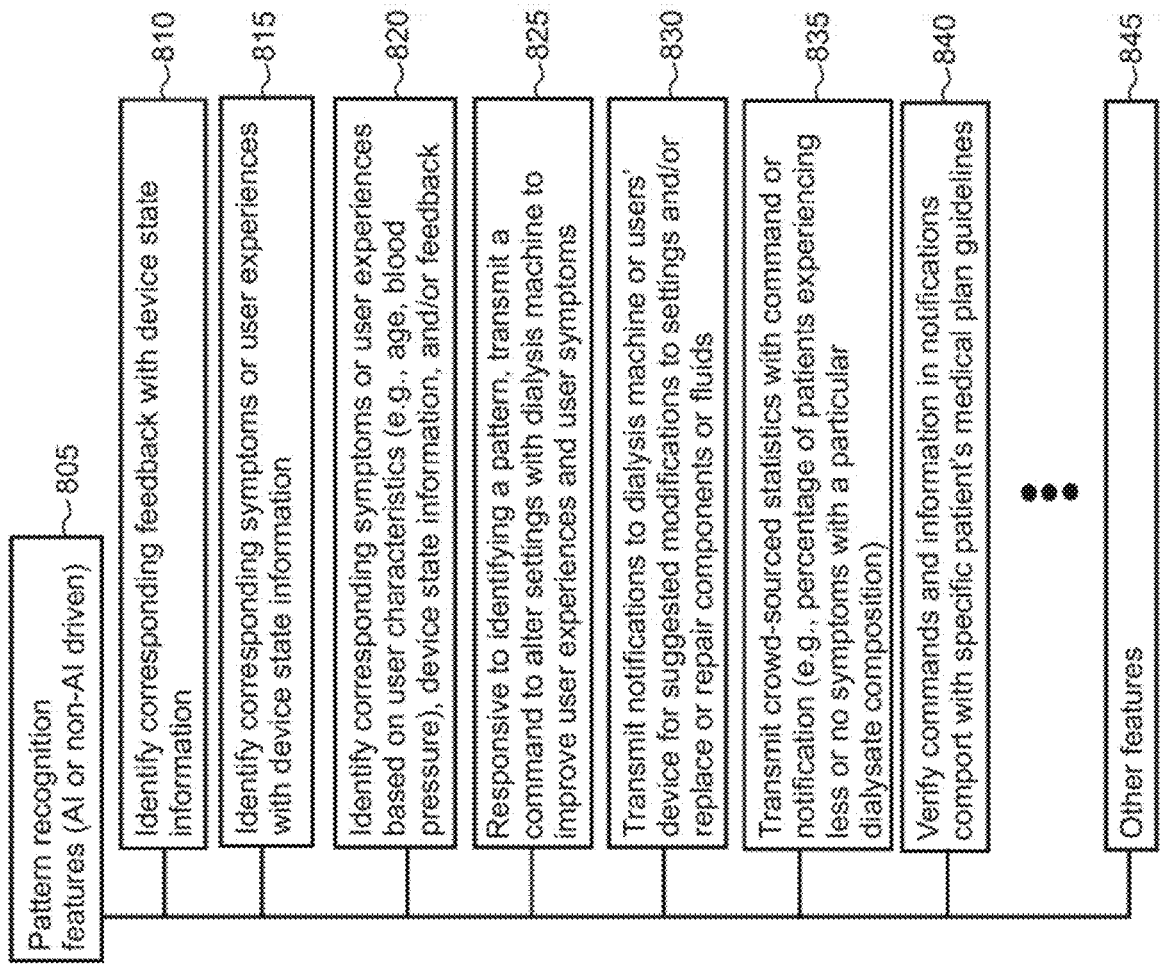
FIG. 8 shows a taxonomy of illustrative pattern recognition features utilized by the remote service.

FIG. 8 shows a taxonomy of pattern recognition features (AI or non-AI driven) that the remote service can perform, as representatively shown by numeral 805. The remote service can identify corresponding feedback with device state information 810; identify corresponding symptoms or user experiences with device state information 815; identify corresponding symptoms or user experiences based on user characteristics (e.g., age, blood, pressure), device state information, and/or feedback 820; responsive to identifying a pattern, transmit a command to alter settings with a dialysis machine to improve user experiences and user symptoms 825; transmit notifications to a dialysis machine or user's device for suggested modifications to settings and/or replace or repair components or fluids 830; transmit crowd-sourced statistics with command or notification (e.g., percentage of patients experiencing less or no symptoms with a particular dialysate composition) 835; verify commands and information in notifications comport with specific patient's medical plan guidelines 840; and other features 845.

Figure 9:
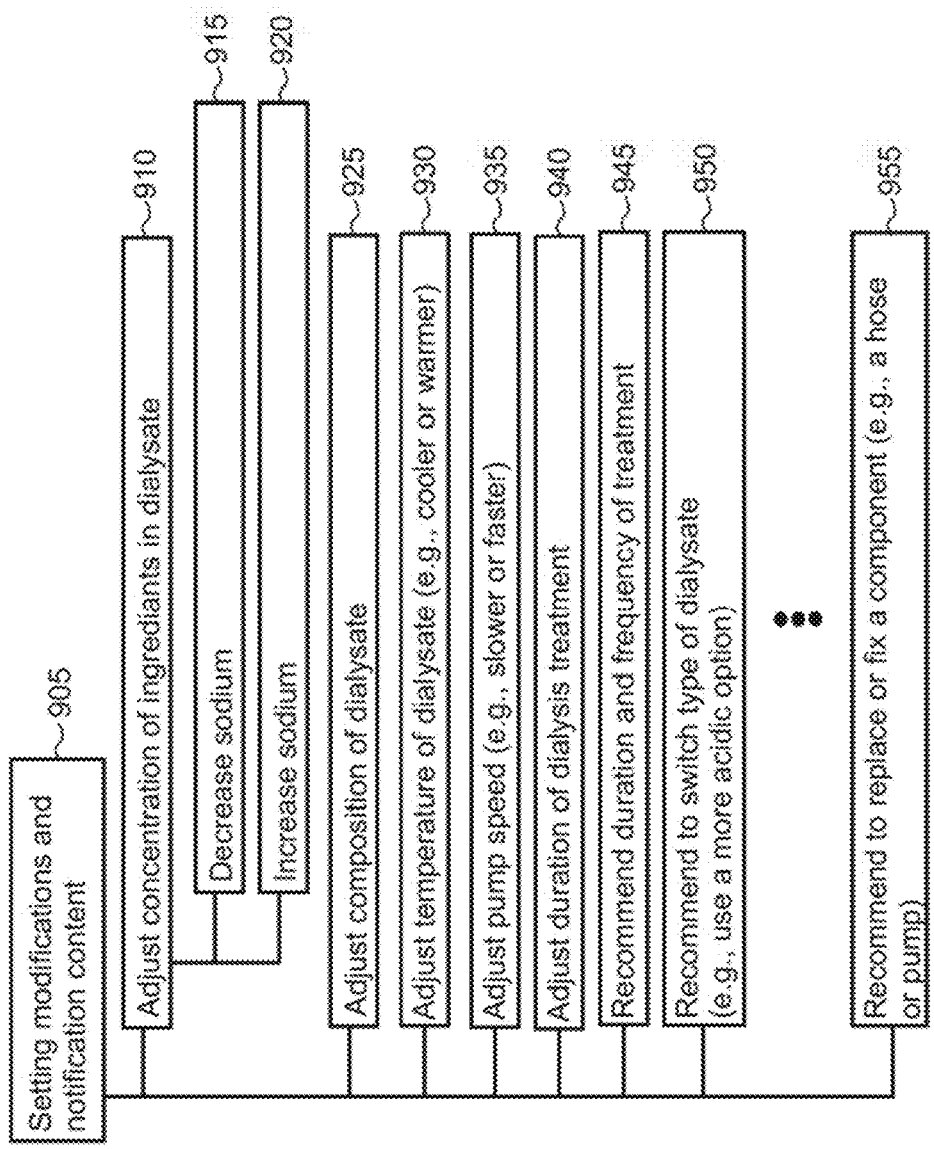
FIG. 9 shows a taxonomy of illustrative setting modifications and notifications transmitted from the remote service to hemodialysis machines.

FIG. 9 shows a taxonomy of setting modifications and notification content that the remote service may transmit to a user's hemodialysis machine or computing device based on the remote service's analysis of received data, as representatively shown by numeral 905. Transmitted setting and notification content can include adjust concentration of ingredients in dialysate 910, which can include decreasing sodium 915 or increasing sodium 920, adjust composition of dialysate 925 (e.g., adjusting one or more of the bicarbonate, acid, or water as typically utilized for dialysate), adjust temperature of dialysate (e.g., cooler or warmer) 930, adjust pump speed (e.g., slower or faster) 935, adjust duration of dialysate treatment 940, recommend duration and frequency of treatment 945, recommend to switch type (e.g., brand or composition) of dialysate 955, or recommend to replace or fix a component (e.g., a hose or pump) 955. Sensors inside the hemodialysis machine may detect component performance in which the remote service, using the crowd sourced data, can recognize that the machine may have a defective component (e.g., hose, pump, etc.) and replacing the component has been associated with increased performance.

Figure 10:
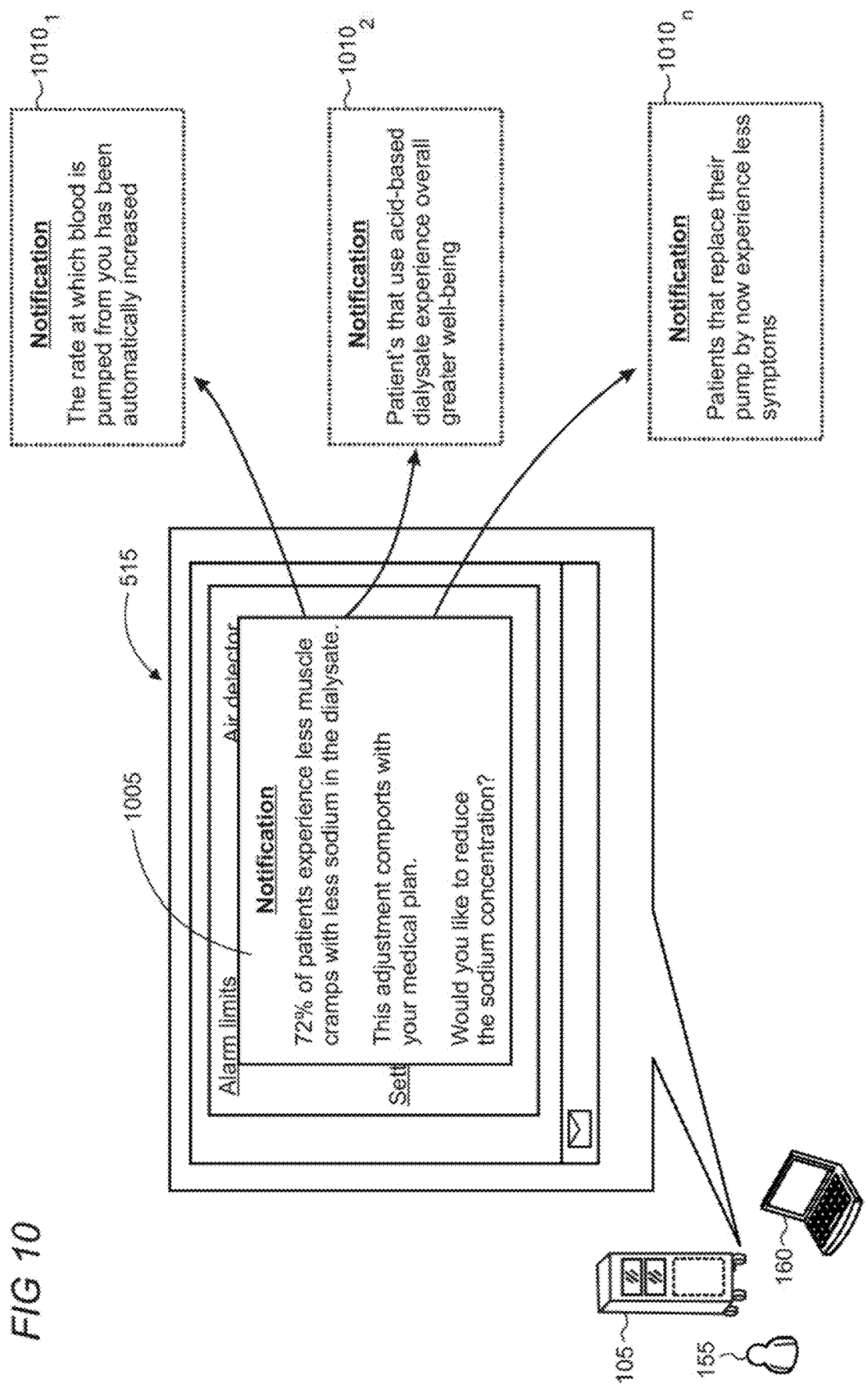
FIG. 10 shows illustrative notifications presented on a display of a user's hemodialysis machine.

FIG. 10 shows an environment of illustrative notifications 1005 and 1010 displayed on a user interface 515 of a hemodialysis machine 105 or computing device 160. Other types of user interfaces can include auditory sounds through speakers, haptic feedback, etc. Notification 1005 explains to the user that he may experience less muscle cramps if he reduces the sodium concentration and, before transmitting the notification, verifies that the recommendation follows the patient's specific medical guidelines and treatment plan. Notifications 1010 each provide unique recommendations to the user to improve their overall well-being and/or improve the machine's performance. While FIG. 10 illustrates the remote service transmitting notifications to the user's device and providing the user the option of making a treatment adjustment, in some scenarios, the remote service can automatically adjust a component or operation of the hemodialysis machine. For example, the remote service can reduce or increase the pump speed if it recognizes that the user's health can be improved by doing so. In some scenarios, the remote service may transmit a notification to the patient that alerts him of the automated adjustment after or upon doing so.

Figure 11:
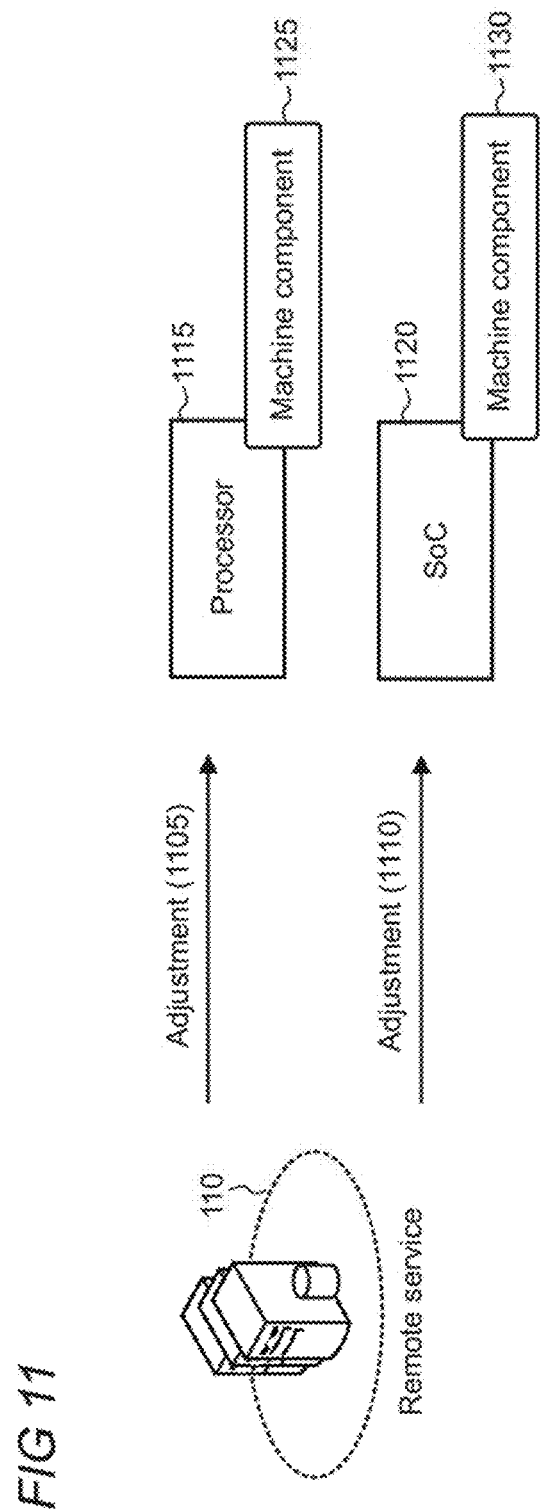
FIG. 11 shows an illustrative environment in which the remote service sends adjustments to a processor or system on a chip (SoC) associated with the hemodialysis machine.

FIG. 11 shows an environment in which the remote service 110 communicates with a processor 1115 or system on a chip (SoC) 1120 associated with and implemented by the hemodialysis machine. The processor or SoC may be associated with one or more distinct machine components 1125, 1130 in order to enable the remote service to transmit an adjustment 1105, 1110 that the hemodialysis machine can execute. For example, the SoC may operate the blood pump and thereby can regulate its flow speed. In some implementations, the SoC may employ one or more sensors to gather data at the hemodialysis machine, and can also be configured to adjust the settings or operations of the same component responsive to, for example, an instructional adjustment from the remote service. As another example, an SoC can control a pump that controls the make of the dialysate, such as by adjusting the bicarbonate, acid, or water.

Figure 12:
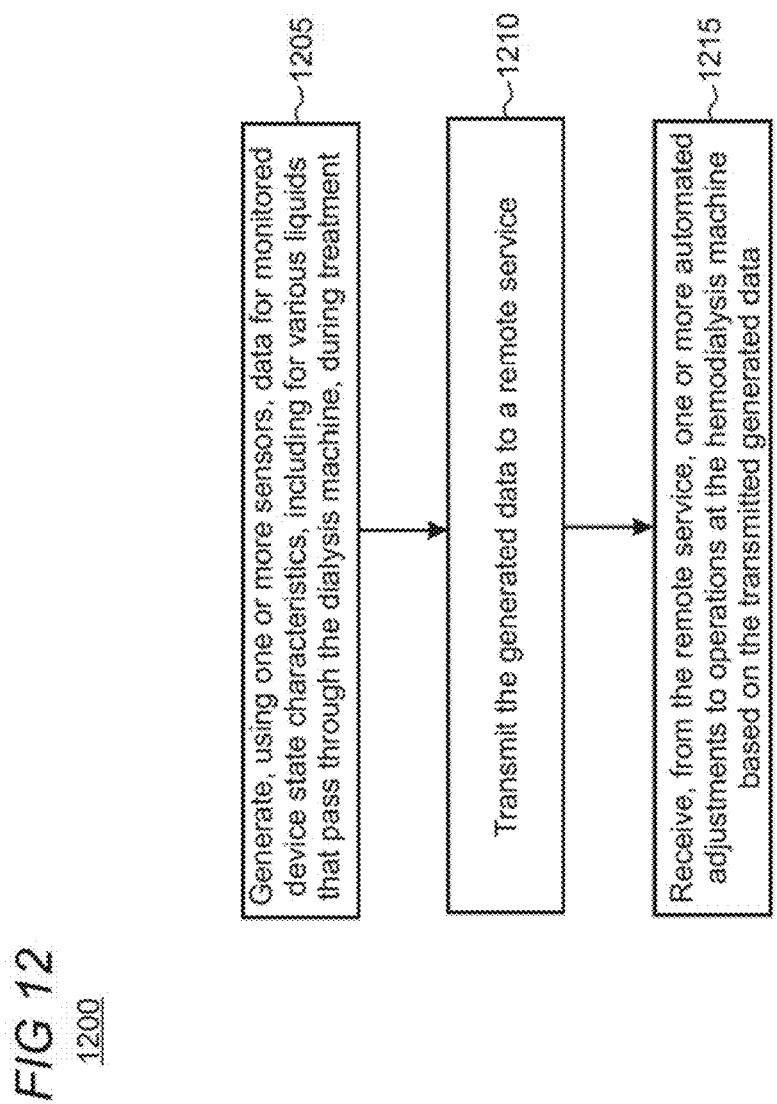
FIGS. 12-14 are flowcharts of illustrative methods performed by a hemodialysis machine, remote service, or computing device.
Figure 13:
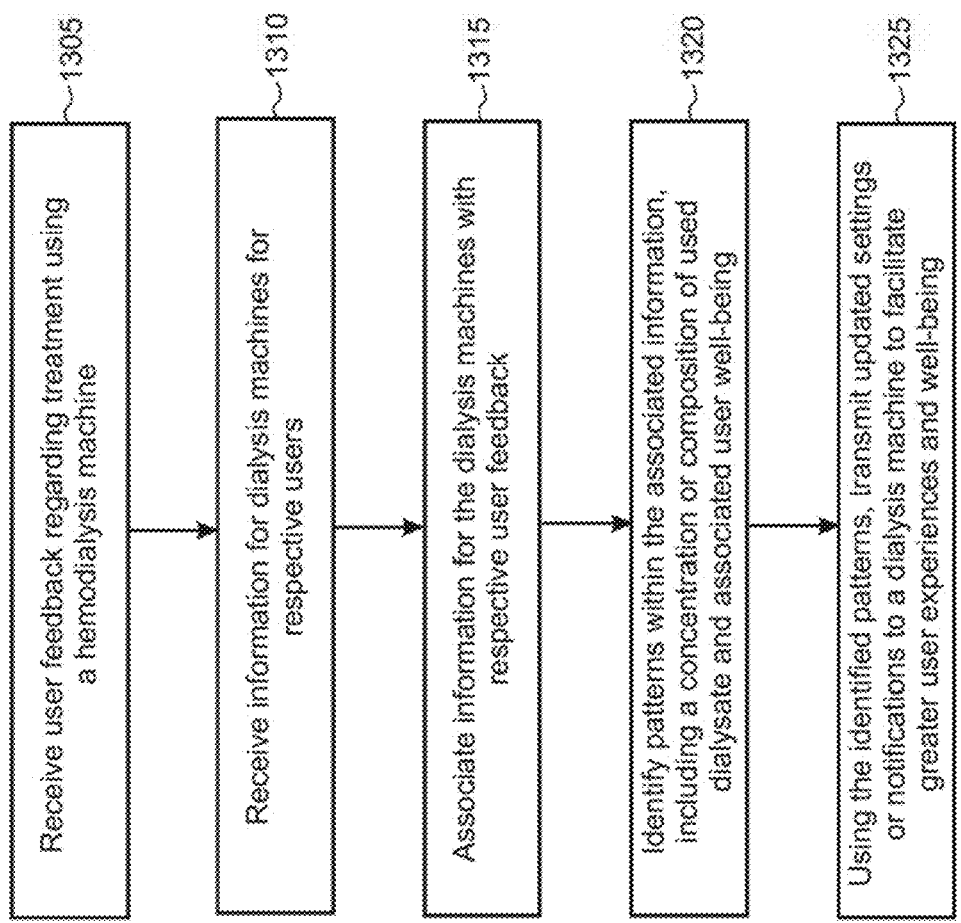
Figure 14:
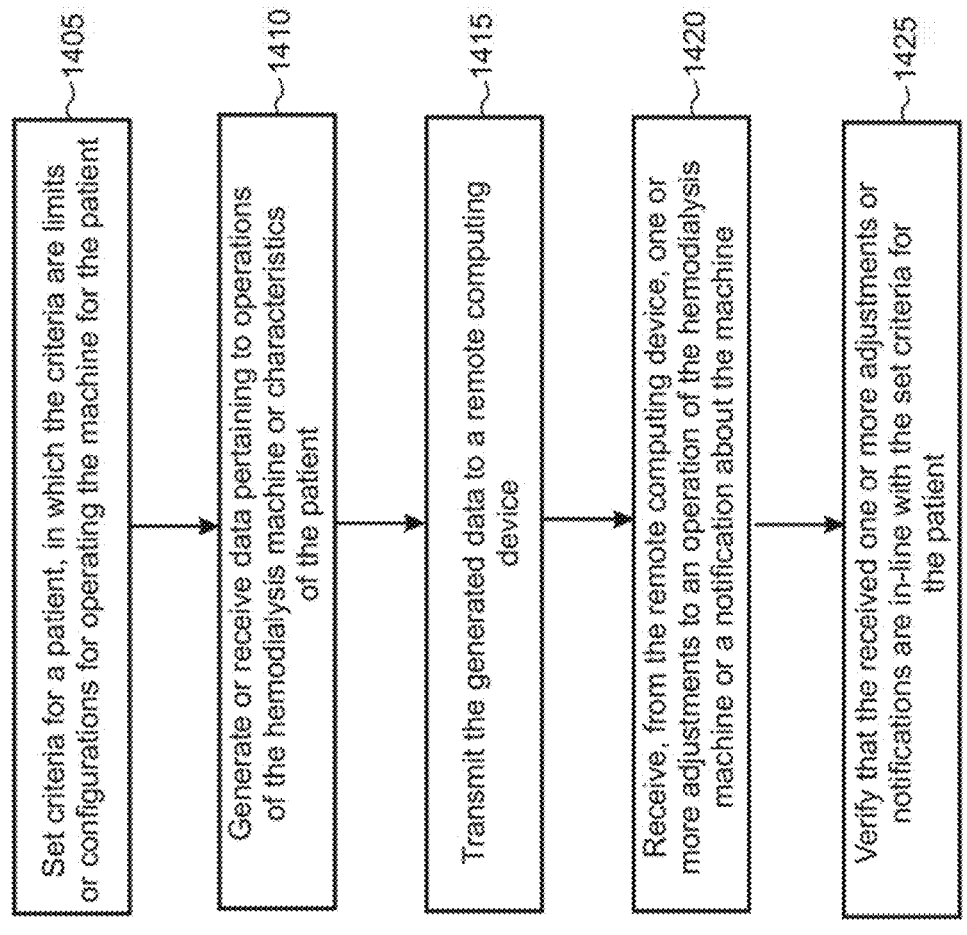

FIGS. 12-14 are flowcharts of exemplary methods 1200, 1300, and 1400 that may be implemented by one or more of a hemodialysis machine, computing device associated with the machine, or a remote service. Unless specifically stated, the methods or steps shown in the flowcharts and described in the accompanying text are not constrained to a particular order or sequence. In addition, some of the methods or steps thereof can occur or be performed concurrently and not all the methods or steps have to be performed in a given implementation depending on the requirements of such implementation and some methods or steps may be optionally utilized.

In step 1205, in FIG. 12, a hemodialysis machine generates, using one or more sensors, data for monitored device state characteristics, including for various liquids that pass through the dialysis machine, during treatment. In step 1210, the hemodialysis machine transmits the generated data to a remote servicer. In step 1215, the hemodialysis machine receives, from the remote service, one or more automated adjustments to operations at the hemodialysis machine based on the transmitted generated data.

FIG. 13 shows a flowchart of a method 1300 which may be performed by a remote service. In step 1305, the remote service user feedback regarding treatment using a hemodialysis machine. In step 1310, the remote service receives information for dialysis machines for respective users. In step 1315, the remote service associates information for the dialysis machine with respective user feedback. In step 1320, the remote service identifies patterns within the associated information, including a concentration or composition of used dialysate and associated user well-being. In step 1325, the remote service, using the identified patterns, transmits updated settings or notifications to a dialysis machine to facilitate greater user experiences and well-being.

FIG. 14 shows a flowchart of a method 1400 which may be performed by a hemodialysis machine or associated computing device. In step 1405, the hemodialysis machine sets criteria for a patient, in which the criteria are limits or configurations for operating the machine for the patient. In step 1410, the hemodialysis machine receives data pertaining to operations of the hemodialysis machine or characteristics of the patient. In step 1415, the hemodialysis machine transmits the received data to a remote computing device. In step 1420, the hemodialysis machine receives, from the remote computing device, one or more adjustments to an operation of the hemodialysis machine or a notification about the machine. In step 1425, the hemodialysis machine verifies that the received one or more adjustments or notifications are in-line with the set criteria for the patient.

Figure 15:
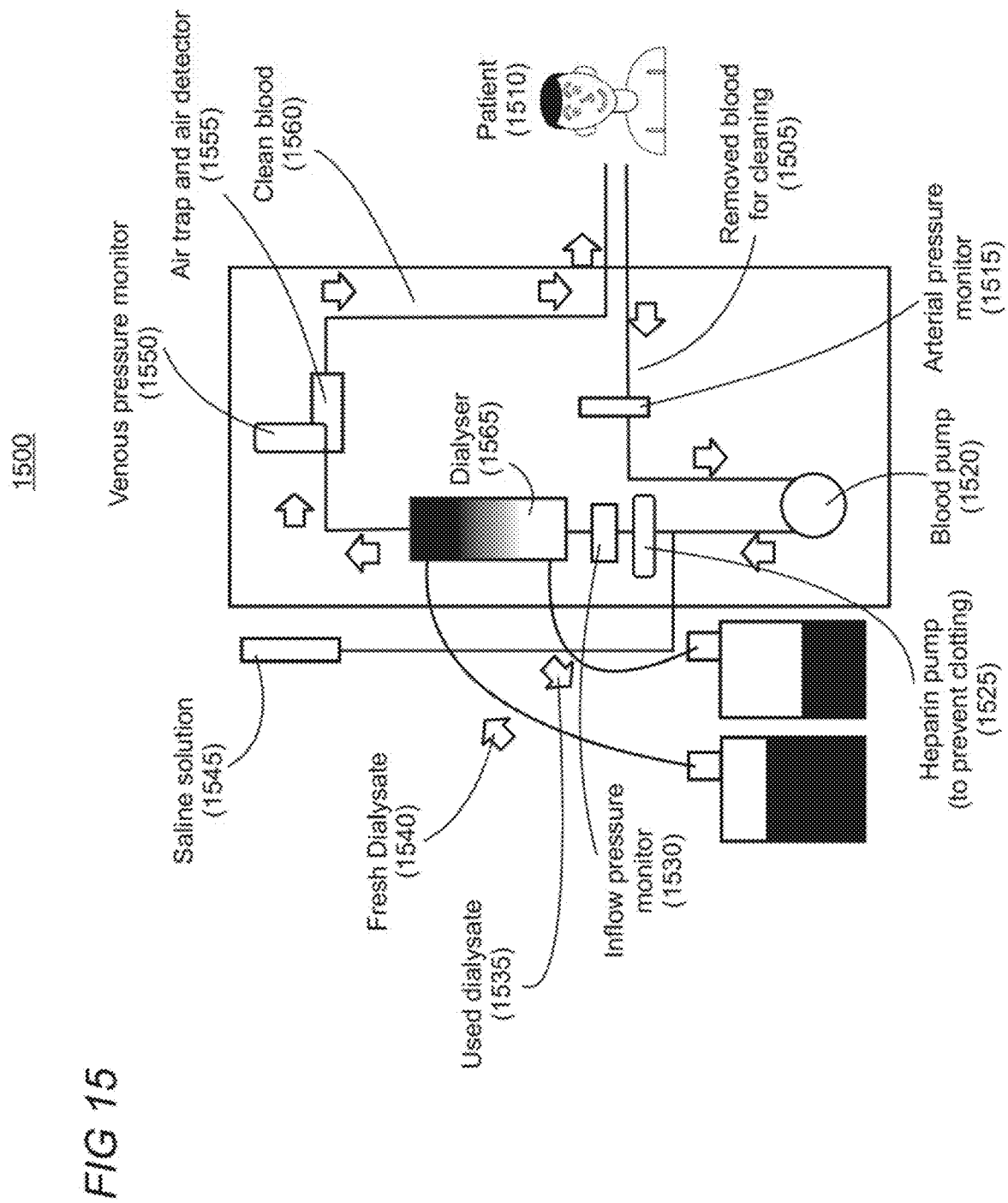
FIG. 15 shows a diagram of an illustrative hemodialysis machine to implement the present automated adjustment of dialysis machine operations.

FIG. 15 is an exemplary hemodialysis machine 1500 which may be implemented and utilized for the purposes described herein. The diagram shows the various components and operations of the hemodialysis machine, but other components not shown are also possible. The hemodialysis machine, using the blood pump 1520, removes blood from the patient 1510, as representatively shown by numeral 1505. An arterial pressure monitor 1515 may be implemented to regulate the amount of pressure and ensure that excessive negative pressure is not generated. A heparin pump 1525 injects a regulated amount of heparin into the blood within the tube while the patient is undergoing treatment. Heparin may be utilized to prevent blood clotting during treatment.

Before entering the dialyzer 1565, the blood flows through an inflow pressure monitor 1530 to regulate the inflow of blood. Saline solution 1545 is can be utilized to flush the system and cleanse the blood which is to be flow back into the patient through the hemodialysis system. The blood enters the dialyzer which is responsible for removing wastes like urea and adding sodium bicarbonate to correct blood acidity. The process by which the dialyzer purifies the blood for bodily use is diffusion, in which the artificial filter of the dialyzer employs fibers, dialysate, and a semi-permeable membrane through which the blood flows. Used dialysate 1535 flows to a waste container and fresh dialysate 1540 is pulled into the dialyzer 1565.

Once the blood advances through the dialyzer 1665, a venous pressure monitor 1550 may be utilized to measure the flow of cleansed blood through the user's vein and into the body. An air trap and air detector 1555 is utilized to make sure no air enters the user's venous needle and vein when moving the cleansed blood back into the user's body. The clean blood 1660 then enters through the user's body through the final portion of the tube, through a needle, and into the user's vein.

Figure 16:
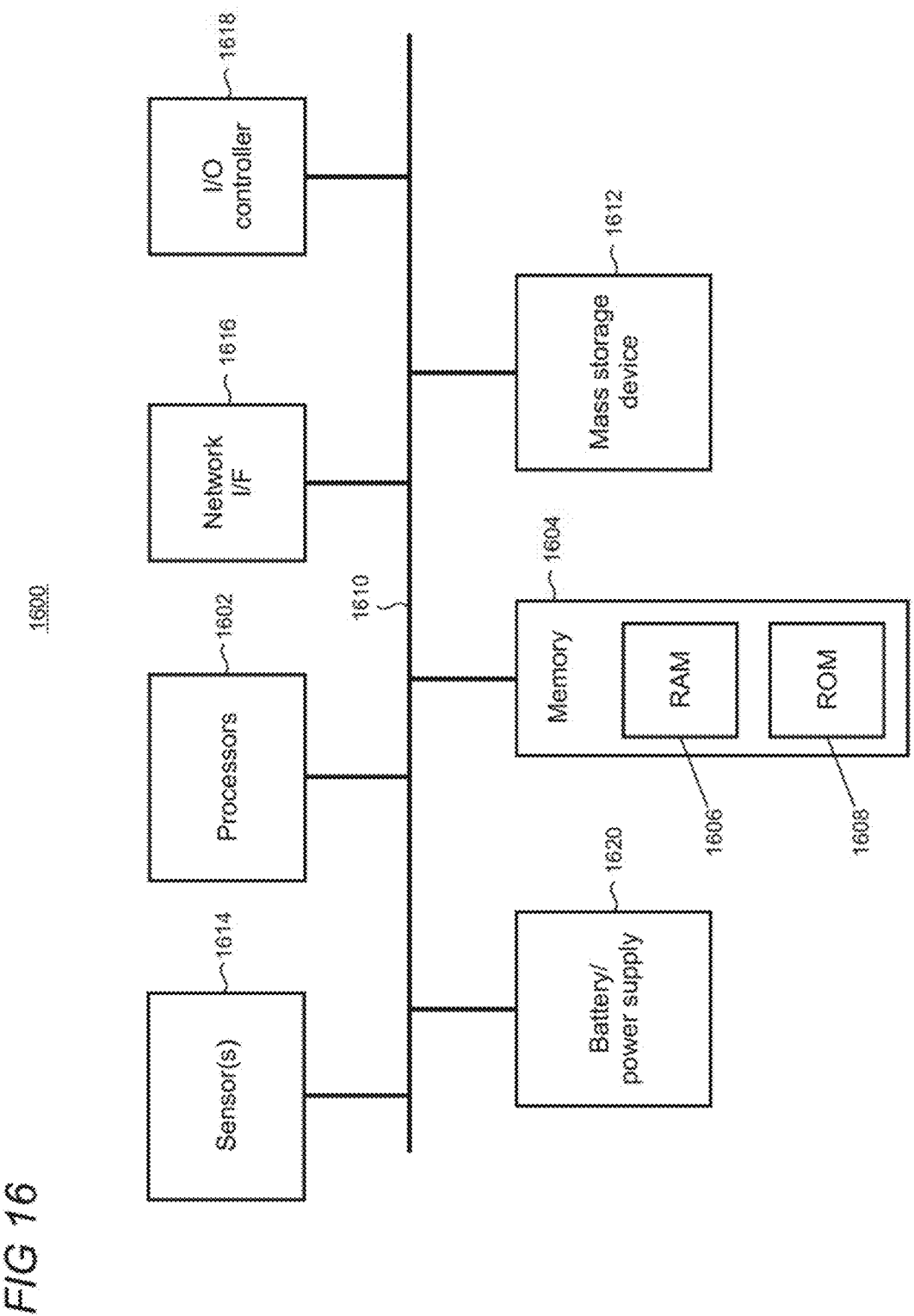
FIG. 16 is a simplified block diagram of an illustrative architecture of a computing device that may be used at least in part to implement the present automated adjustment of dialysis machine operations.

FIG. 16 shows an illustrative architecture 1600 for a client computing device such as a laptop computer or personal computer for the present automated adjustment of dialysis machines. The architecture 1600 illustrated in FIG. 16 includes one or more processors 1602 (e.g., central processing unit, dedicated Artificial Intelligence chip, graphics processing unit, etc.), a system memory 1604, including RAM (random access memory) 1606 and ROM (read only memory) 1608, and a system bus 1610 that operatively and functionally couples the components in the architecture 1600. A basic input/output system containing the basic routines that help to transfer information between elements within the architecture 1600, such as during startup, is typically stored in the ROM 1608. The architecture 1600 further includes a mass storage device 1612 for storing software code or other computer-executed code that is utilized to implement applications, the file system, and the operating system. The mass storage device 1612 is connected to the processor 1602 through a mass storage controller (not shown) connected to the bus 1610. The mass storage device 1612 and its associated computer-readable storage media provide non-volatile storage for the architecture 1600. Although the description of computer-readable storage media contained herein refers to a mass storage device, such as a hard disk or CD-ROM drive, it may be appreciated by those skilled in the art that computer-readable storage media can be any available storage media that can be accessed by the architecture 1600.

By way of example, and not limitation, computer-readable storage media may include volatile and non-volatile, removable and non-removable media implemented in any method or technology for storage of information such as computer-readable instructions, data structures, program modules, or other data. For example, computer-readable media includes, but is not limited to, RAM, ROM, EPROM (erasable programmable read only memory), EEPROM (electrically erasable programmable read only memory), Flash memory or other solid state memory technology, CD-ROM, DVD, HD-DVD (High Definition DVD), Blu-ray, or other optical storage, magnetic cassette, magnetic tape, magnetic disk storage or other magnetic storage device, or any other medium which can be used to store the desired information and which can be accessed by the architecture 1600.

According to various embodiments, the architecture 1600 may operate in a networked environment using logical connections to remote computers through a network. The architecture 1600 may connect to the network through a network interface unit 1616 connected to the bus 1610. It may be appreciated that the network interface unit 1616 also may be utilized to connect to other types of networks and remote computer systems. The architecture 1600 also may include an input/output controller 1618 for receiving and processing input from a number of other devices, including a keyboard, mouse, touchpad, touchscreen, control devices such as buttons and switches or electronic stylus (not shown in FIG. 16). Similarly, the input/output controller 1618 may provide output to a display screen, user interface, a printer, or other type of output device (also not shown in FIG. 16).

It may be appreciated that the software components described herein may, when loaded into the processor 1602 and executed, transform the processor 1602 and the overall architecture 1600 from a general-purpose computing system into a special-purpose computing system customized to facilitate the functionality presented herein. The processor 1602 may be constructed from any number of transistors or other discrete circuit elements, which may individually or collectively assume any number of states. More specifically, the processor 1602 may operate as a finite-state machine, in response to executable instructions contained within the software modules disclosed herein. These computer-executable instructions may transform the processor 1602 by specifying how the processor 1602 transitions between states, thereby transforming the transistors or other discrete hardware elements constituting the processor 1602.

Encoding the software modules presented herein also may transform the physical structure of the computer-readable storage media presented herein. The specific transformation of physical structure may depend on various factors in different implementations of this description. Examples of such factors may include, but are not limited to, the technology used to implement the computer-readable storage media, whether the computer-readable storage media is characterized as primary or secondary storage, and the like. For example, if the computer-readable storage media is implemented as semiconductor-based memory, the software disclosed herein may be encoded on the computer-readable storage media by transforming the physical state of the semiconductor memory. For example, the software may transform the state of transistors, capacitors, or other discrete circuit elements constituting the semiconductor memory. The software also may transform the physical state of such components in order to store data thereupon.

As another example, the computer-readable storage media disclosed herein may be implemented using magnetic or optical technology. In such implementations, the software presented herein may transform the physical state of magnetic or optical media, when the software is encoded therein. These transformations may include altering the magnetic characteristics of particular locations within given magnetic media. These transformations also may include altering the physical features or characteristics of particular locations within given optical media to change the optical characteristics of those locations. Other transformations of physical media are possible without departing from the scope and spirit of the present description, with the foregoing examples provided only to facilitate this discussion.

The architecture 1600 may further include one or more sensors 1614 or a battery or power supply 1620. The sensors may be coupled to the architecture to pick up data about an environment or a component, including temperature, pressure, etc. Exemplary sensors can include a thermometer, accelerometer, smoke or gas sensor, pressure sensor (barometric or physical), light sensor, ultrasonic sensor, gyroscope, among others. The power supply may be adapted with an AC power cord or a battery, such as a rechargeable battery for portability.

In light of the above, it may be appreciated that many types of physical transformations take place in the architecture 1600 in order to store and execute the software components presented herein. It also may be appreciated that the architecture 1600 may include other types of computing devices, including wearable devices, handheld computers, embedded computer systems, smartphones, PDAs, and other types of computing devices known to those skilled in the art. It is also contemplated that the architecture 1600 may not include all of the components shown in FIG. 16, may include other components that are not explicitly shown in FIG. 16, or may utilize an architecture completely different from that shown in FIG. 16.

Figure 17:
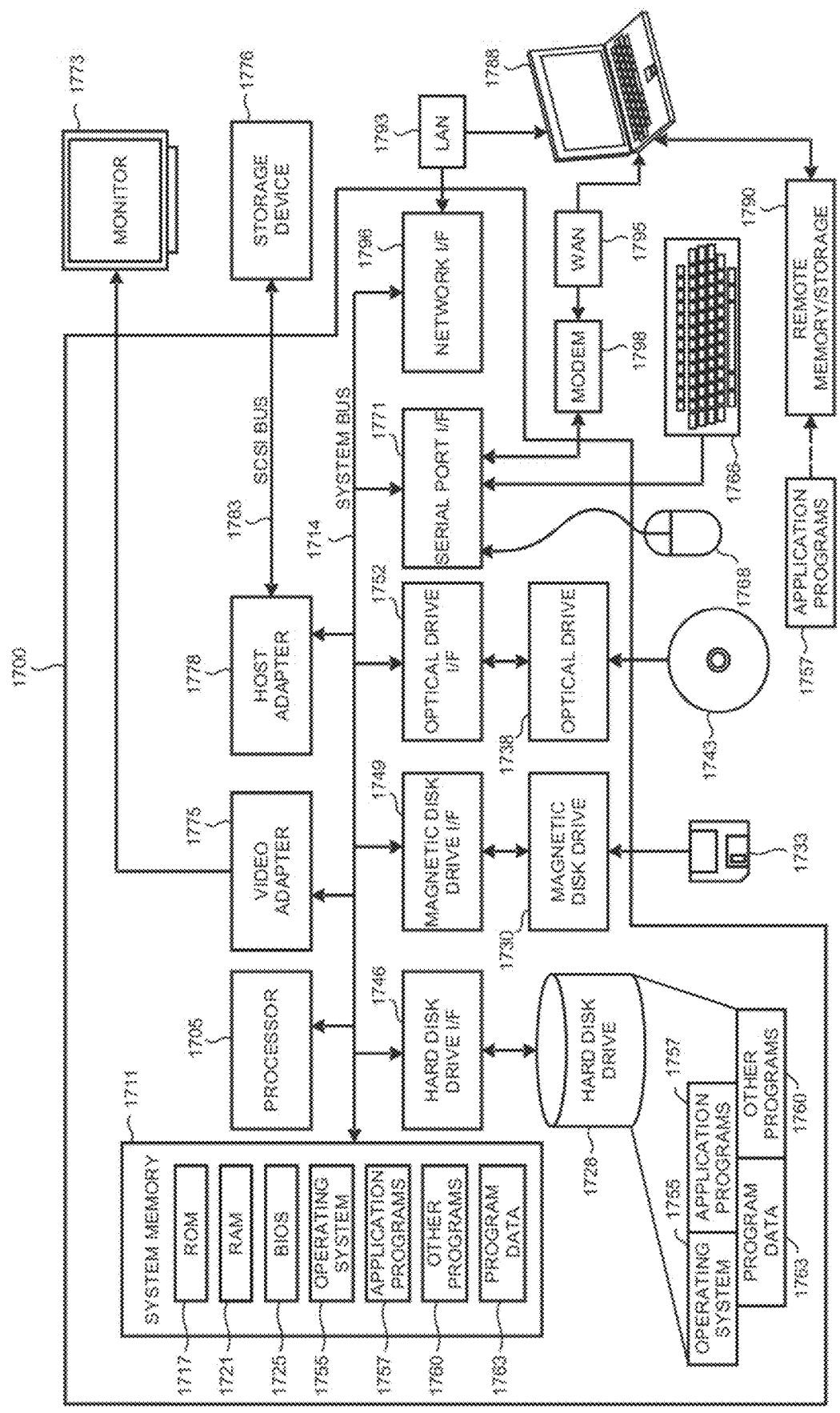
FIG. 17 is a simplified block diagram of an illustrative remote computing device, remote service, or computer system that may be used in part to implement the present automated adjustment of dialysis machine operations.

FIG. 17 is a simplified block diagram of an illustrative computer system 1700 such as a PC or server with which the present automated adjustment of dialysis machines may be implemented. Computer system 1700 includes a processor 1705, a system memory 1711, and a system bus 1714 that couples various system components including the system memory 1711 to the processor 1705. The system bus 1714 may be any of several types of bus structures including a memory bus or memory controller, a peripheral bus, or a local bus using any of a variety of bus architectures. The system memory 1711 includes read only memory (ROM) 1717 and random-access memory (RAM) 1721. A basic input/output system (BIOS) 1725, containing the basic routines that help to transfer information between elements within the computer system 1700, such as during startup, is stored in ROM 1717. The computer system 1700 may further include a hard disk drive 1728 for reading from and writing to an internally disposed hard disk (not shown), a magnetic disk drive 1730 for reading from or writing to a removable magnetic disk 1733 (e.g., a floppy disk), and an optical disk drive 1738 for reading from or writing to a removable optical disk 1743 such as a CD (compact disc), DVD (digital versatile disc), or other optical media. The hard disk drive 1728, magnetic disk drive 1730, and optical disk drive 1738 are connected to the system bus 1714 by a hard disk drive interface 1746, a magnetic disk drive interface 1749, and an optical drive interface 1752, respectively. The drives and their associated computer-readable storage media provide non-volatile storage of computer-readable instructions, data structures, program modules, and other data for the computer system 1700. Although this illustrative example includes a hard disk, a removable magnetic disk 1733, and a removable optical disk 1743, other types of computer-readable storage media which can store data that is accessible by a computer such as magnetic cassettes, Flash memory cards, digital video disks, data cartridges, random access memories (RAMs), read only memories (ROMs), and the like may also be used in some applications of the present automated adjustment of dialysis machines. In addition, as used herein, the term computer-readable storage media includes one or more instances of a media type (e.g., one or more magnetic disks, one or more CDs, etc.). For purposes of this specification and the claims, the phrase "computer-readable storage media" and variations thereof, are intended to cover non-transitory embodiments, and do not include waves, signals, and/or other transitory and/or intangible communication media.

A number of program modules may be stored on the hard disk, magnetic disk 1733, optical disk 1743, ROM 1717, or RAM 1721, including an operating system 1755, one or more application programs 1757, other program modules 1760, and program data 1763. A user may enter commands and information into the computer system 1700 through input devices such as a keyboard 1766 and pointing device 1768 such as a mouse. Other input devices (not shown) may include a microphone, joystick, game pad, satellite dish, scanner, trackball, touchpad, touchscreen, touch-sensitive device, voice-command module or device, user motion or user gesture capture device, or the like. These and other input devices are often connected to the processor 1705 through a serial port interface 1771 that is coupled to the system bus 1714, but may be connected by other interfaces, such as a parallel port, game port, or universal serial bus (USB). A monitor 1773 or other type of display device is also connected to the system bus 1714 via an interface, such as a video adapter 1775. In addition to the monitor 1773, personal computers typically include other peripheral output devices (not shown), such as speakers and printers. The illustrative example shown in FIG. 17 also includes a host adapter 1778, a Small Computer System Interface (SCSI) bus 1783, and an external storage device 1776 connected to the SCSI bus 1783.

The computer system 1700 is operable in a networked environment using logical connections to one or more remote computers, such as a remote computer 1788. The remote computer 1788 may be selected as another personal computer, a server, a router, a network PC, a peer device, or other common network node, and typically includes many or all of the elements described above relative to the computer system 1700, although only a single representative remote memory/storage device 1790 is shown in FIG. 17. The logical connections depicted in FIG. 17 include a local area network (LAN) 1793 and a wide area network (WAN) 1795. Such networking environments are often deployed, for example, in offices, enterprise-wide computer networks, intranets, and the Internet.

When used in a LAN networking environment, the computer system 1700 is connected to the local area network 1793 through a network interface or adapter 1796. When used in a WAN networking environment, the computer system 1700 typically includes a broadband modem 1798, network gateway, or other means for establishing communications over the wide area network 1795, such as the Internet. The broadband modem 1798, which may be internal or external, is connected to the system bus 1714 via a serial port interface 1771. In a networked environment, program modules related to the computer system 1700, or portions thereof, may be stored in the remote memory storage device 1790. It is noted that the network connections shown in FIG. 17 are illustrative and other means of establishing a communications link between the computers may be used depending on the specific requirements of an application of the present automated adjustment of dialysis machines.

Exemplary systems, devices, and methods are disclosed herein. In one embodiment, a dialysis machine configured to automatically adjust operations, comprising: a network interface; one or more sensors local to the dialysis machine; one or more processors operatively coupled to the network interface and one or more sensors; and a hardware-based memory device having executable instructions which, when executed by the one or more processors, cause the dialysis machine to: generate, using the one or more sensors, data for monitored device state characteristics, including for various liquids that pass through the dialysis machine during a treatment session with a user; transmit the generated data to a remote service; and receive from the remote service one or more automated adjustments to operations at the hemodialysis machine based on the transmitted generated data, in which the received one or more adjustments include adjusting a concentration or composition of dialysate or saline solution utilized during the hemodialysis treatment to calibrate an administered dosage.

In another example, the adjusted operations occurs after multiple different hemodialysis treatments. As another example, the remote service or hemodialysis machine verifies that the automated adjustment comports with treatment criteria for the patient. As another example, the remote service transmits the automated adjustment after identifying patterns using artificial intelligence processing of received data, and in which the transmitted automated adjustment is assessed based on the artificial intelligence processing of the data. As another example, the automated adjustment is unique to the user and is determined using known physiological information about the user in combination with the generated sensor data. As another example, the automated adjustment is further determined using crowd-source information derived from dialysis machines during patient uses. As another example, the dialysis machine or a computing device associated with the user of the dialysis machine is configured to receive user feedback for their treatment, and the user feedback is transmitted to the remote service in determining the adjusted operations for the hemodialysis machine.

Another exemplary embodiment includes a method performed by a remote service in communication with a dialysis machine, comprising: receiving user feedback regarding treatment using a hemodialysis machine; receiving information for dialysis machines for respective users; associating information for the dialysis machines with respective user feedback; identifying patterns within the associated information, including a concentration or composition of used dialysate and associated user well-being; and using the identified patterns, transmitting updated settings or notifications to a dialysis machine to facilitate greater user experiences and well-being.

As another example, the user feedback is received pre-treatment, post-treatment, or during treatment. As another example, the updated settings or notifications include any one or more of adjusting a concentration or composition of a dialysate; adjusting pump pressure to increase or decrease a rate at which blood is pumped from the user; adjust rate at which filtration is performed; a notification on a user interface to change water filter; or a notification on the user interface to change a dialysate membrane. As another example, the user interface includes any one or more of a visualization on a display screen, an auditory sound using a speaker, haptic feedback, or a gesture. As another example, the user feedback includes user-experienced symptoms pre-treatment and during the treatment, and general well-being of the user. As another example, types of user feedback can include user responses to a questionnaire including multiple choice and fill-in the blank, free-form user information, and a rating system. As another example, information and feedback are received from a plurality of users, pattern identification includes identifying operational settings for the hemodialysis machine and its operational components for users experiencing positive or general well-being based on the feedback, and further comprising using the pattern identifications, transmitting the updated settings or notifications to the dialysis machine using the identified operational settings for the user's experiencing positive or general well-being. As another example, information and feedback are received from a plurality of users, and pattern determination includes identifying operational settings for the hemodialysis machine and its operational components for users experiencing negative or poor well-being, and further comprising: using the pattern determinations, transmitting updated settings and notifications to the hemodialysis machine to preemptively address operational settings which correspond to negative experiences or poor well-being for users.

In another embodiment, one or more hardware-based non-transitory computer-readable memory devices stored within a hemodialysis machine that is configured to filter blood from a patient, the memory devices including instructions which, when executed by one or more processors, cause the hemodialysis machine to: set criteria for a patient, in which the criteria are limits or configurations for operating the machine for the patient; receive data pertaining to operations of the hemodialysis machine or characteristics of the patient, in which the received data is received from the patient or generated by the hemodialysis machine; transmit the received data to a remote computing device; receive, from the remote computing device, one or more adjustments to an operation of the hemodialysis machine or a notification about the hemodialysis machine or the patient, wherein the remote computing device determines the one or more adjustments using an artificial intelligence (AI) engine based on crowd-sourced data obtained from at least other hemodialysis patients; and verifying that the received one or more adjustments or notification are in-line with the set criteria for the patient.

In another example, the AI engine of the remote computing device trains a model of data and deploys a predictive model to determine the one or more automated adjustments for the hemodialysis machine. As another example, the generated or received data include information for processed blood or dialysate or pump operation. As another example, a received adjustment includes adjusting a concentration or composition of dialysate or sodium solution utilized during a dialysis treatment to calibrate an administered dosage, or adjusting pump pressure. As another example, the one or more adjustments or notification is derived from crowd-sourced information for dialysis treatments associated with respective users that are relatable and applicable to the patient.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A dialysis machine configured to automatically adjust operations, comprising:
   a network interface;
   one or more sensors local to the dialysis machine;
   one or more processors operatively coupled to the network interface and one or more sensors; and
   a hardware-based memory device having executable instructions which, when executed by the one or more processors, cause the dialysis machine to:
      generate, using the one or more sensors, data for monitored device state characteristics, including for various liquids that pass through the dialysis machine during a treatment session with a user, in which the various liquids include at least blood and dialysate;
      transmit the generated data to a remote service; and
      receive from the remote service one or more automated adjustments to operations at the dialysis machine based on the transmitted generated data, in which the received one or more adjustments include adjusting a dialysis machine operation,
         in which the remote service transmits the automated adjustment after identifying specific patterns within the received data,
         wherein the specifically identified patterns are based on multiple treatment sessions and multiple distinct patients, and the patterns include at least an operational configuration of dialysis machines for the multiple distinct patients and how those operational configurations correspond to the respective patient's experiences derived from individual patient feedback, wherein the patient feedback is physically and manually entered by the patient or a caregiver and received at an input device on the dialysis machine or a computing device associated with the dialysis machine.

2. The dialysis machine of claim 1, in which the adjusted operations occurs after multiple different dialysis treatments.

3. The dialysis machine of claim 1, wherein the executable instructions further cause the dialysis machine to:
   set treatment criteria for the patient, the treatment criteria being limits or configurations in the dialysis machine operations for the patient, in which the remote service or dialysis machine verifies that the automated adjustment comports with the set treatment criteria for the patient.

4. The dialysis machine of claim 1, in which the automated adjustment is unique to the user and is determined using known physiological information about the user in combination with the generated sensor data.

5. A method performed by a remote service in communication with a dialysis machine, comprising:
   receiving user feedback regarding treatment using a dialysis machine, wherein the remote service receives multiple sets of user feedback data from multiple distinct users;
   receiving information for dialysis machines for respective users;
   associating the information for the dialysis machines with respective user feedback, in which the user feedback includes an indication as to the respective user's well-being input by the users and received by respective dialysis machines or associated computing devices;
   identifying specific patterns using the associated information collectively among the users, in which the patterns include identifying user well-being characteristics based on a concentration or composition of used dialysate for each user; and using the identified patterns, transmitting an updated setting or notification to a dialysis machine to facilitate greater user experiences and well-being.

6. The method of claim 5, in which the user feedback is received pre-treatment, post-treatment, or during treatment.

7. The method of claim 6, in which the updated setting or notification include any one or more of adjusting a concentration or composition of a dialysate; adjusting pump pressure to increase or decrease a rate at which blood is pumped from the user; adjust rate at which filtration is performed; a notification on a user interface to change water filter; or a notification on the user interface to change a dialysate membrane.

8. The method of claim 7, in which the user interface includes any one or more of a visualization on a display screen, an auditory sound using a speaker, haptic feedback, or a gesture.

9. The method of claim 5, in which the user feedback includes user-experienced symptoms pre-treatment and during the treatment, and general well-being of the user.

10. The method of claim 5, in which types of user feedback can include user responses to a questionnaire including multiple choice and fill-in the blank, free-form user information, and a rating system.

11. The method of claim 5, in which:
information and feedback are received from a plurality of users,
pattern identification includes identifying operational settings for the dialysis machine and its operational components for users experiencing positive or general well-being based on the feedback, and further comprising:
using the pattern identifications, transmitting the updated setting or notification to the dialysis machine using the identified operational settings for the user's experiencing positive or general well-being.

12. The method of claim 5, in which:
information and feedback are received from a plurality of users, and
pattern identification includes identifying operational settings for the dialysis machine and its operational components for users experiencing negative or poor well-being, and further comprising:
using the pattern identifications, transmitting updated settings and notifications to the dialysis machine to preemptively address operational settings which correspond to negative experiences or poor well-being for users.

13. One or more hardware-based non-transitory computer-readable memory devices stored within a hemodialysis machine that is configured to filter blood from a patient, the memory devices including instructions which, when executed by one or more processors, cause the hemodialysis machine to:
set criteria for a patient, in which the criteria are limits or configurations for operating the hemodialysis machine for the patient;
receive data pertaining to operations of the hemodialysis machine or characteristics of the patient, in which the received data is received from the patient or generated by the hemodialysis machine;
transmit the received data to a remote computing device;
receive, from the remote computing device, one or more adjustments to an operation of the hemodialysis machine or a notification about the hemodialysis machine or the patient, wherein the remote computing device determines the one or more adjustments using an artificial intelligence (AI) engine based on crowd-sourced data obtained from at least other hemodialysis patients operating distinct and respective hemodialysis machines, in which the one or more adjustments are at least partially determined based on identified commonalities among the hemodialysis patients or their hemodialysis machines; and
verifying that the received one or more adjustments or notification are in-line with the set criteria for the patient.

14. The one or more hardware-based computer-readable memory devices of claim 13, in which the AI engine of the remote computing device trains a model of data and deploys a predictive model to determine the one or more automated adjustments for the hemodialysis machine.

15. The one or more hardware-based computer-readable memory devices of claim 13, in which the generated or received data includes information for processed blood or dialysate, or pump operation.

16. The one or more hardware-based computer-readable memory devices of claim 13, in which a received adjustment includes adjusting a concentration or composition of dialysate or sodium solution utilized during a dialysis treatment to calibrate an administered dosage, or adjusting pump pressure.

17. The one or more hardware-based computer-readable memory devices of claim 13, in which the one or more adjustments or notification is derived from crowd-sourced information for dialysis treatments associated with respective users that are relatable and applicable to the patient.

* * * * *